United States Patent [19]

Greenwald

[11] 4,150,228

[45] Apr. 17, 1979

[54] THIOETHER SUBSTITUTED SILVER HALIDE SOLVENTS

[75] Inventor: Richard B. Greenwald, Cambridge, Mass.

[73] Assignee: Polaroid Corporation, Cambridge, Mass.

[21] Appl. No.: 811,712

[22] Filed: Jun. 30, 1977

Related U.S. Application Data

[60] Division of Ser. No. 686,587, May 14, 1976, abandoned, which is a continuation-in-part of Ser. No. 563,306, Apr. 1, 1975, abandoned, which is a continuation-in-part of Ser. No. 463,263, Apr. 23, 1974, abandoned.

[51] Int. Cl.[2] .......................................... C07D 239/24

[52] U.S. Cl. .................................. 544/302; 544/309; 544/314; 96/66 HD

[58] Field of Search .................... 260/251 R; 544/302, 544/309, 314

[56] References Cited

U.S. PATENT DOCUMENTS 2,487,569 11/1947 MacKey ......................... 260/251 R

FOREIGN PATENT DOCUMENTS 472526 3/1951 Canada ............................... 260/251 R

*Primary Examiner*—Nicholas S. Rizzo

*Attorney, Agent, or Firm*—Sybil A. Campbell

[57] ABSTRACT

The present invention is concerned with novel compounds useful as photographic silver halide complexing agents and with their photographic use. The subject compounds are represented by the formulas

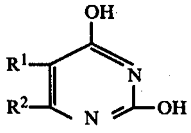

and

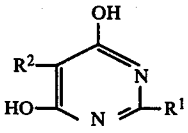

wherein one of $R^1$ and $R^2$ is $(CH_2)_xSR^3$ and the other of said $R^1$ and $R^2$ is $(CH_2)_ySR^3$ wherein $R^3$ is alkyl, x is a whole number 0 or 1 and y is a whole number from 0 to 5.

19 Claims, No Drawings

THIOETHER SUBSTITUTED SILVER HALIDE SOLVENTS

CROSS-REFERENCE TO RELATED PATENT APPLICATIONS

This application is a division of my copending application Ser. No. 686,587 filed May 14, 1976, now abandoned, which is a continuation-in-part of my application Ser. No. 563,306 filed Apr. 1, 1975, now abandoned, which, in turn, is a continuation-in-part of my application Ser. No. 463,263 filed Apr. 23, 1974, now abandoned.

BACKGROUND OF THE INVENTION

1. Field of the Invention

This invention relates to photographic products, processes and compositions employing a new class of silver halide solvents, and in a particular aspect, it is concerned with novel compounds useful as silver halide solvents and with the photographic use thereof.

2. Description of the Prior Art

Photographic processing compositions capable of forming water-soluble complex silver salts are known to be useful in many types of silver halide photography. To obtain a relatively stable image in an exposed and developed photosensitive silver halide emulsion, the silver halide remaining in the unexposed and undeveloped areas of the emulsion should be converted to a soluble silver complex that can be removed by washing or converted to a stable silver complex that will not "print-out" upon prolonged exposure to light. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photographic processes. Such processes are now well known in the art; see for example, U.S. Pat. Nos. 2,543,181; 2,647,056; 2,983,606, etc. In processes of this type, an exposed silver halide emulsion is treated with a processing composition whereby the exposed silver halide emulsion is developed and an image-wise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

Various compounds have been employed as silver halide solvents in the photographic processes described above. One of the most commonly employed is sodium thiosulfate. Other silver halide solvents that have been used include thiocyanates, such as potassium and sodium thiocyanate; and cyclic imides, such as barbituric acid and uracil.

The present invention is concerned with a new class of silver halide solvents useful in both conventional and diffusion transfer photography and with novel compounds useful as photographic silver halide solvents.

SUMMARY OF THE INVENTION

It is, therefore, the primary object of the present invention to provide photographic products, processes and compositions employing a new class of silver halide solvents.

It is another object of the present invention to provide novel compounds useful as silver halide solvents and to provide photographic products, processes and compositions employing the same.

It is a further object of the present invention to provide a novel intermediate useful in the synthesis of said novel compounds.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

According to the present invention, it has been found that difunctional compounds wherein one of said functions is a hard or soft atom that ionizes to the corresponding anion in alkaline solution for combining with silver cation and the other of said functions is a non-ionizable soft base for additionally combining with said silver cation form silver complexes soluble in alkaline solution and are useful for complexing undeveloped silver halide in photographic processes. These compounds may be aliphatic, cyclic and acyclic, or they may be aromatic.

The hard-soft [HSAB] principle that "hard acids prefer to bind to hard bases and soft acids prefer to bind to soft bases" is now well-known, and its application and usefulness in understanding a variety of chemical phenomena has been widely discussed notably by R. G. Pearson, J. Am. Chem. Soc. 85, 3533(1963); Chemistry in Britain 3,103(1967); and J. Chem. Education 45,581(1968). Under "The Principle of Hard and Soft Acids and Bases", a "soft base" is defined as one in which the valence electrons of the donor atom are easily distorted or removed as opposed to a "hard base" in which the valence electrons of the donor atom are tightly held. A "soft acid" is one in which the acceptor atom generally is large in size and has several valence electrons which are easily distorted or removed, and a "hard acid" is one in which the acceptor atom is small in size and does not contain unshared pairs of electrons in the valence shell, i.e., does not contain valence electrons that are easily distorted or removed. Because of these properties, hard acids and hard bases exhibit high electronegativity and low polarizability, and conversely, soft acids and soft bases exhibit low electronegativity and high polarizability. The acids and bases may be an atom, molecule or ion, with cations, for example, being acids. Under the HSAB principle, silver cation ($Ag^+$) is classified as a soft acid, and thus, prefers to coordinate with a soft base, i.e., the complexes of $Ag^+$ with soft donor atoms will generally be more stable than those with hard donor atoms. As a general rule, soft acids coordinate best to one of the heavier atoms of a family of elements so that the general order of stabilities of complexes A:B wherein A is a soft acid are:

N<<P>As>Sb>Bi

O<<S~Se~Te

As noted above, in the subject difunctional compounds the ionizable atom may be a hard atom as exemplified by O which ionizes to the corresponding $O^{\ominus}$ anion in basic solution, or it may be a soft atom as exemplified by C which ionizes to the corresponding $C^{\ominus}$ in basic solution. It will be appreciated that the difunctional compound selected will possess a hard or soft atom that ionizes at the pH at which the particular photographic process is performed. The non-ionizable soft base for additionally combining with the silver cation may be, for example, an —As<, —P<, —Se—, or —S— containing moiety.

In a preferred embodiment of the present invention, the difunctional compounds comprise an aliphatic or aromatic molecule containing as the ionizable atom, an O, N or C atom possessing a proton removable in alkali to provide the corresponding $O^{\ominus}$, $N^{\ominus}$ or $C^{\ominus}$ anion, and containing as the non-ionizable soft base, a moiety, i.e., a group containing —S—, excluding —SH groups that would form $—S^{\ominus}$ in alkali. The position of —S— with respect to that of the anion should be such that the —S— is capable of combining with the silver cation together with the anion. In general, the —S— is adjacent to or up to 6 atoms away from the anion. Where the compound comprises an aromatic molecule, the position of —S— ordinarily is one atom up to 6 atoms away from the anion. Where the compound comprises an aliphatic molecule, the position of —S— ordinarily is adjacent to or 2 atoms up to 6 atoms away from the anion.

Preferred —S— containing moieties are thioether groups, particularly $T—(X)_n—$ wherein T represents R—S— or

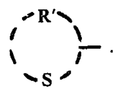

Compounds substituted with the preferred thioether group may be represented by the formula $M—(X)_n—T$ wherein M represents an aliphatic or aromatic moiety, Y—A, wherein A is an atom selected from O, N and C ionizable in alkaline solution to the corresponding anion $O^{\ominus}$, $N^{\ominus}$ and $C^{\ominus}$ and Y represents the residue of said moiety; T represents R—S— or

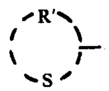

wherein R is a monovalent hydrocarbon radical, cyclic including aliphatic or aromatic, and acyclic including carbon atoms forming a continuous or a branched chain and R' represents the atoms necessary to complete an aromatic or aliphatic ring; X represents a methylene group; and n is a whole number preferably from 0 to 5 so that the —S— of said thioether group is in a position alpha, beta, gamma, delta, epsilon or zeta to said anion. Preferably, R is a monovalent aliphatic radical including cyclic and acyclic aliphatic radicals, e.g., alkyl and cycloalkyl, such as, methyl, ethyl, isopropyl, t-butyl, cyclopentyl and cyclohexyl, and R' represents the carbon atoms to complete a 5- or 6-membered ring, e.g., aromatic, such as, 2-thienyl

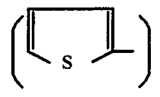

or aliphatic, such as, 2-thianyl

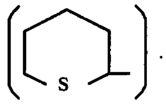

The compounds may be substituted with more than one thioether group provided that at least one thioether group is appropriately positioned with respect to an anion. Preferably, the compounds possess one or two thioether groups as represented by the formula $M—[(X)_n—T]_m$ wherein m is 1 or 2 and M, X, T and n have the same meaning given above.

Examples of aromatic compounds possessing the said ionizable atom which may be substituted with said thioether group(s) include 2,4-dihydroxypyrimidine (uracil), 4,6-dihydroxypyrimidine (pseudouracil), hydroxy-substituted 1,3,5-triazines, hydroxy-substituted 1,2,4-triazines, 1,2,3,4-tetrazole, 3,6-dihydroxypyridazine, 5-pyrazolone and 4-hydroxyquinazoline. Examples of aliphatic compounds possessing the said ionizable atom which may be substituted with said thioether group(s) include sulfonamido derivatives of amino acids, 1,3-disulfonylalkanes, 1,3-disulfonylcycloalkanes and alkanes containing a sulfonyl group and a cyano, a sulfinyl or a t-sulfonamido group separated from the sulfonyl group by a single carbon substituted with at least one hydrogen atom.

The appropriate positioning of the $T—(X)_n—$ group, as exemplified by $R—S—(X)_n—$, with respect to the anion of the moiety M is illustrated below wherein $A^{\ominus}$ represents the anion $O^{\ominus}$, $N^{\ominus}$ or $C^{\ominus}$ and Y represents the residue of the molecule:

| | |
|---|---|
| $[Y—A^{\ominus}]$-S—R | alpha |
| $[Y—A^{\ominus}]$-X—S—R | beta |
| $[Y—A^{\ominus}]$-X—X—S—R | gamma |
| $[Y—A^{\ominus}]$-X—X—X—S—R | delta |
| $[Y—A^{\ominus}]$-X—X—X—X—S—R | epsilon |
| $[Y—A^{\ominus}]$X—X—X—X—X—S—R | zeta |

For both aliphatic and aromatic compounds, the —S— preferably is gamma to the anion, for example, $$-\underset{|}{C}^{\ominus}-\underset{\alpha}{CH_2}-\underset{\beta}{CH_2}-\underset{\gamma}{S}-R.$$

In a particularly preferred embodiment, the R of the R—S—$(X)_n$— group is alkyl and the group is alkylthio- or alkylthioalkylene-, and the R' of said

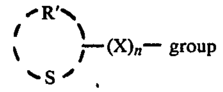

represents the carbons to complete 2-thienyl. It will be appreciated that these groups may be substituted with, for example, solubilizing groups, such as carboxy, hydroxy or amino.

Particularly useful silver halide complexing agents within the broad class of compounds described above are 2,4-dihydroxypyrimidines(uracils) and 4,6-dihydroxypyrimidines (pseudo uracils) substituted on at least one carbon atom with an —S-containing moiety, preferably the above-denoted thioether group, T—$(X)_n$—, as shown in the following formulas:

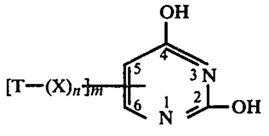

(A)

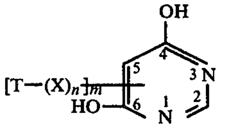

(B)

wherein said T—$(X)_n$— is substituted in the 5- and/or 6-position in formula A and is substituted in the 2- and/or 5-position in formula B and T, X and n have the same meaning given above.

Preferred compounds of this type are 2,4-dihydroxypyrimidines substituted in the 5- or 6-position with said thioether group and 4,6-dihydroxypyrimidines substituted in the 2- or 5-position with said thioether group as shown in the following formulas:

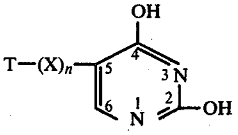

(I)

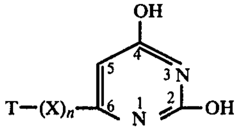

(II)

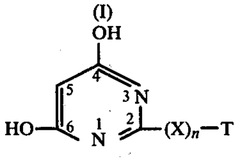

(III)

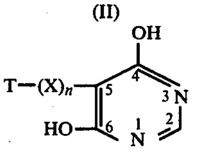

(IV)

It will be appreciated that the uracils and pseudo uracils in addition to the thioether substituent, may be substituted on the remaining carbon atom with groups, such as, halo, hydroxy, amino, alkyl and alkyl substituted with, e.g., solubilizing groups, such as hydroxy, carboxy, amino and aliphatic ethers.

Particularly preferred compounds of this type are those of the following formulas:

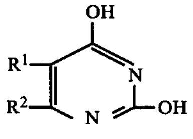

(V)

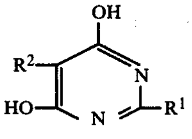

(VI)

wherein one of $R^1$ and $R^2$ is $-(CH_2)_xSR^3$ and the other of said $R^1$ and $R^2$ is $-(CH_2)_ySR^3$ wherein $R^3$ is alkyl, x is a whole number 0 or 1 and y is a whole number from 0 to 5. The alkyl group $R^3$ may be substituted, usually in the omega position, with a solubilizing group, such as, carboxy, hydroxy or amino, and preferably, $R^3$ is lower alkyl containing 1 to 4 carbon atoms, particularly $-(CH_2)_zCH_2R^4$ wherein z is a whole number 0 to 3 and $R^4$ represents a solubilizing group. The compounds of formulas V and VI represent the novel compounds of the present invention.

Specific examples of compounds useful as silver halide solvents in accordance with the present invention include:

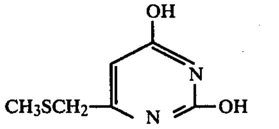

(1)

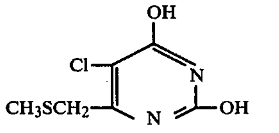

(2)

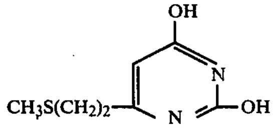

(3)

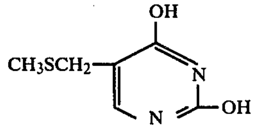

(4)

-continued
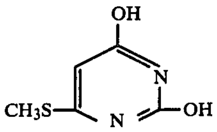
(5)
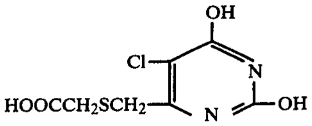
(6)
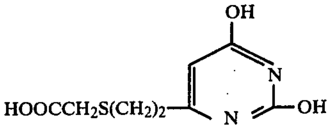
(7)
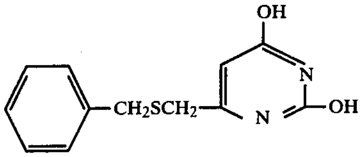
(8)
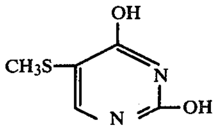
(9)
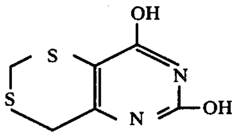
(10)
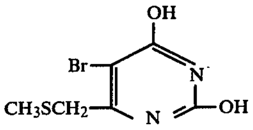
(11)
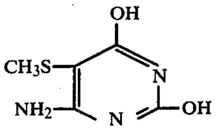
(12)
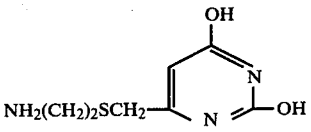
(13)
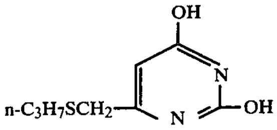
(14)
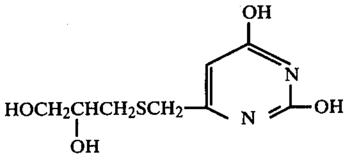
(15)
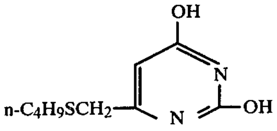
(16)
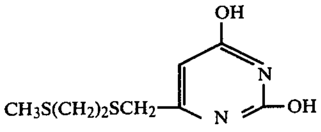
(17)

-continued
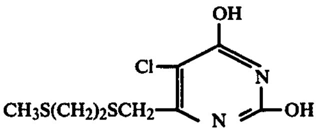
(18)
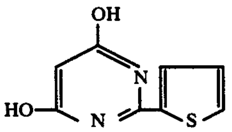
(19)
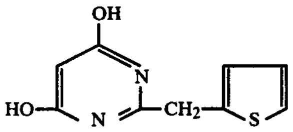
(20)
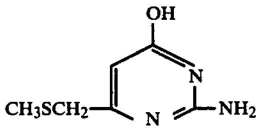
(21)
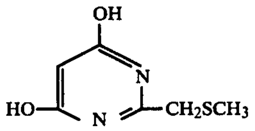
(22)
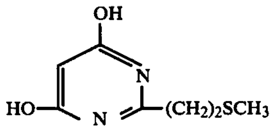
(23)
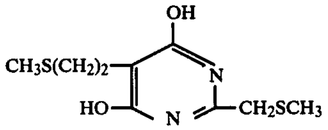
(24)
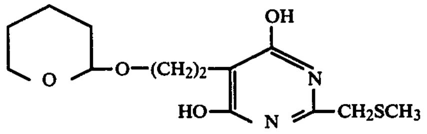
(25)
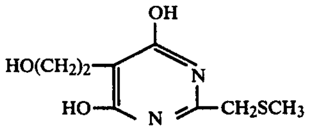
(26)
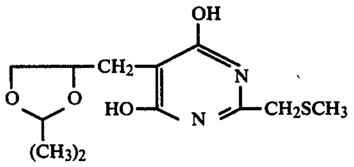
(27)
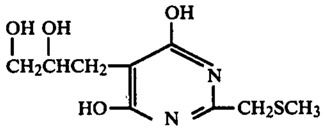
(28)
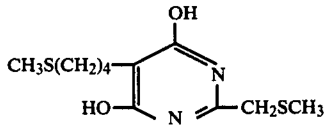
(29)
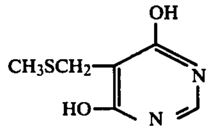
(30)

-continued
(31)
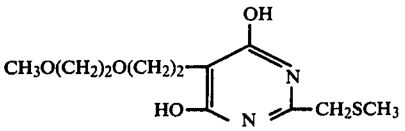
(32)
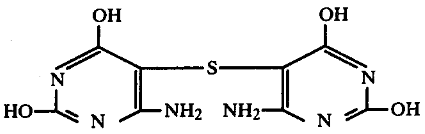
(33)
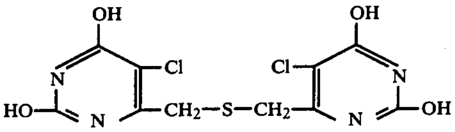
(34)
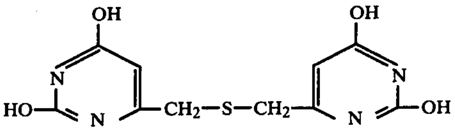
(35)
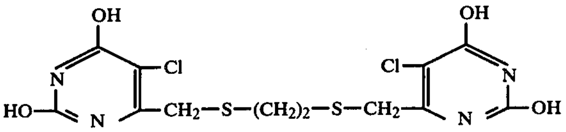
(36)
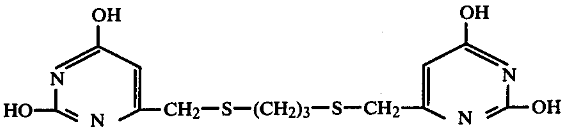
(37)
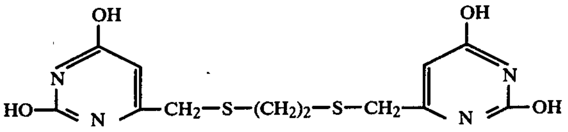
(38)
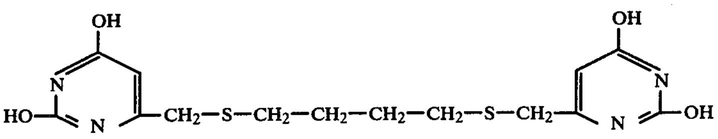
(39)
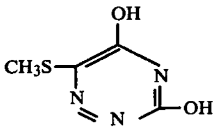
(40)
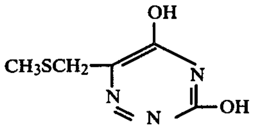
(41)
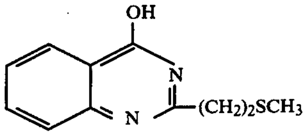
(42)
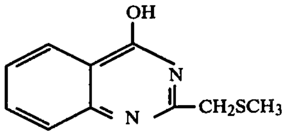
(43)
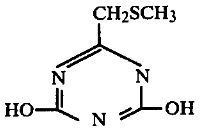

-continued
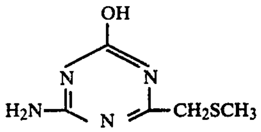
(44)
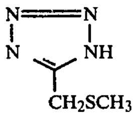
(45)
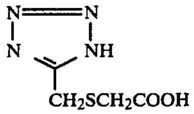
(46)
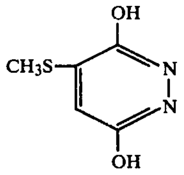
(47)
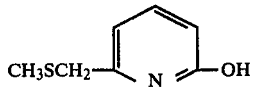
(48)
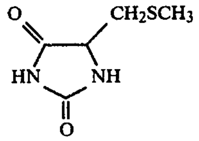
(49)
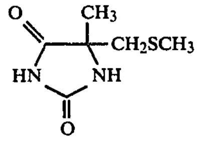
(50)
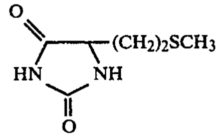
(51)
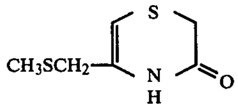
(52)
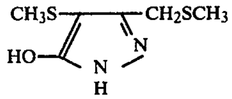
(53)
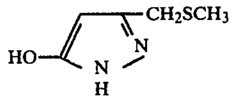
(54)
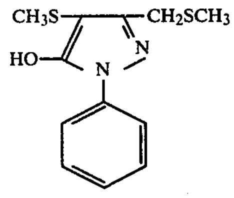
(55)
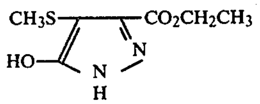
(56)

-continued
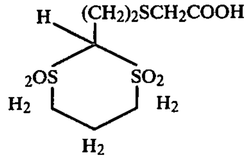
(57)
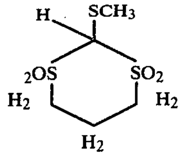
(58)
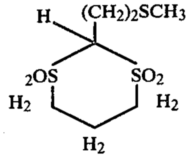
(59)
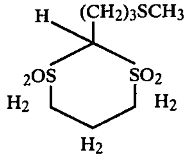
(60)
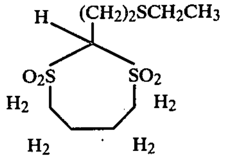
(61)
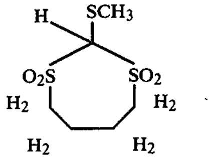
(62)
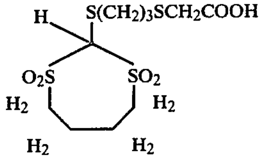
(63)
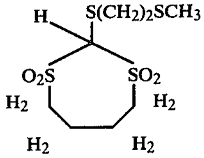
(64)
$CH_3SO_2CHSO_2CH_3$
$CH_2CH_2SCH_3$
(65)
$CH_3SO_2CHSOCH_3$
$CH_2CH_2SCH_3$
(66)
$CH_3SO_2CHCN$
$CH_2CH_2CH_2SCH_3$
(67)
$CH_3SO_2CHCN$
$CH_2CH_2SCH_3$
(68)
(69)
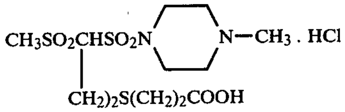
(70)
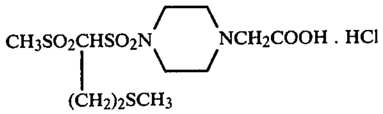

-continued
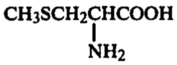
(71)
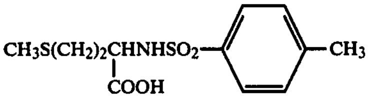
(72)
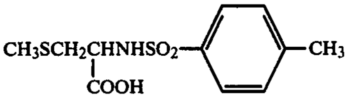
(73)
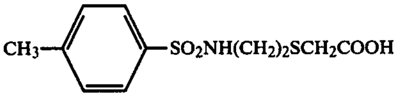
(74)
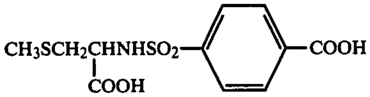
(75)
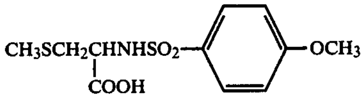
(76)
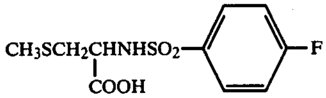
(77)
$CH_3SO_2NH(CH_2)_2SCH_2COOH$ (78)
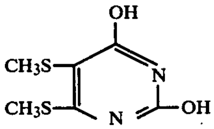
(79)
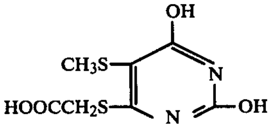
(80)
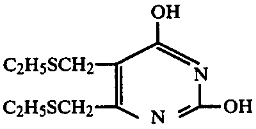
(81)
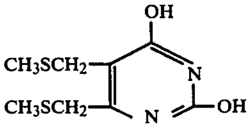
(82)
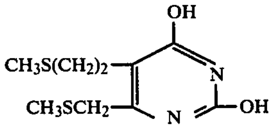
(83)
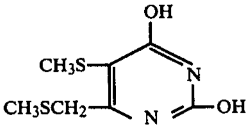
(84)
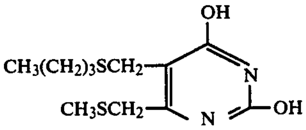
(85)
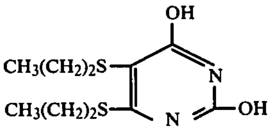
(86)

-continued

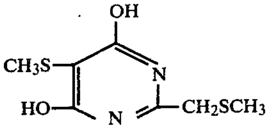
(87)

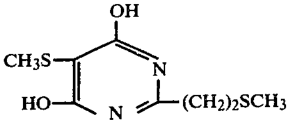
(88)

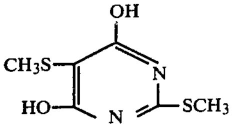
(89)

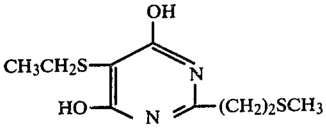
(90)

The thioether-substituted 2,4-dihydroxypyrimidines (uracils) may be prepared, for example, by reacting a 5- or 6-mercaptoalkyl-substituted 2,4-dihydroxypyrimidine with a halide, e.g., RI or RCl, to give the corresponding RS-alkyl-substituted compound or by reacting a 5- or 6-haloalkyl-substituted 2,4-dihydroxypyrimidine with a mercaptan, RSH, to give the corresponding RS-alkyl-substituted compound, using the procedure reported by Giner-Sorolla et al., J. Med. Chem. 9, 97 (1966). These compounds also may be prepared by reaction of the appropriate β-keto esters, e.g.,

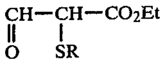
and
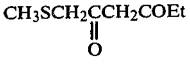
with thiourea,

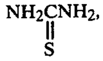

followed by alkylation and acid hydrolysis. These procedures are similar to those reported by M. Jackman et al., J. Amer. Chem. Soc. 70, p. 497 (1948) and R. M. Dodson et al., ibid., 72, p. 3281 (1950). The thioether-substituted 4,6-dihydroxypyrimidines (pseudo uracils) may be prepared, for example, by reacting an RS-substituted amidine,

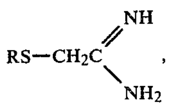
, with a diethyl malonate, $R'CH(CO_2Et)_2$ using the procedures described in J. Chem. Soc. 1943, p. 388; J. Org. Chem. 18, p. 653; and J. Org. Chem. 17, p. 1320. The pseudo uracils also may be prepared using the procedure of Gershon et al., J. Org. Chem. 26, 1874 to prepare the 5-bromomethyl-4,6-dichloropyrimidine and then displacing the bromo group with a mercaptide, $RS^{\ominus}M^{\oplus}$, followed by acid hydrolysis to the dihydroxy product.

Uracil and pseudo uracil sulfides may be prepared, for example, by reacting chloro- and mercapto-substituted uracils, such as, 5- (or 6-) chloromethyluracil and 5- (or 6-) mercaptomethyluracil as described in the aforementioned Giner-Sorolla reference. The bis uracils, such as, those of formulas 35 to 38, may be synthesized by reacting chloromethyl-substituted uracils with a dithiol, such as, 1,2-ethanedithiol or 1,3-propanedithiol. Mercapto-substituted hydroxy and/or amino pyrimidines also can be alkylated with an alkyl halide in alcoholic solution of sodium alkoxide or with chloroalkanoic acids using the procedures described in The Chemistry of Heterocyclic Compounds, Vol. 16, p. 282–83, A. Weissberger, Wiley-Interscience 1962. Various other procedures for preparing thioether-substituted uracils and pseudo uracils and their sulfides and other -S-containing derivatives are described in the latter reference and in Supplement 1 of Vol. 16 (1970). Uracils with cyclic thioether moieties bonded to adjacent carbon atoms may be prepared from the corresponding hydroxy/mercapto-substituted compounds by treating with chloroacetic acid as described in the J. Amer. Chem. Soc. 82, p. 158 (1960).

The thioether-substituted symmetrical triazines may be prepared, for example, from the haloalkyl-substituted dihydroxy or amino/hydroxy triazine by reaction with the sodium derivative of a mercaptan, $RS^{\ominus}Na^{\oplus}$, using the procedure reported by M. A. Stevens et al., J. Heterocyclic Chem. 4, 268 (1967). Chloroalkyl-substituted dihydroxy sym. triazines useful for reaction with the mercaptide may be prepared using the procedure reported in the J. Amer. Chem. Soc., 79, p. 944. The thioether-substituted asymmetrical triazine compounds may be prepared from 6-mercapto-3,5-dihydroxy (or hydroxy/amino)1,2,4-triazines using the procedure described by C. Cristescu et al., Pharmazie 17(4), p. 209 (1962).

Thioether-substituted tetrazoles may be prepared by reacting a nitrile, e.g., $RSCH_2CN$ with $NaN_3$, by alkylation of a 5-mercapto tetrazole; or by reacting a 5-haloalkyltetrazole with a mercaptan, RSH. The thioether-substituted 5-pyrazolones may be prepared by reacting an (R-thio) acetoacetic acid ester and hydrazine or substituted hydrazines using the procedure reported by Gundermann et al., Ber. 95, 2076 (1962). The thioether-substituted 3,6-dihydroxypyridazines may be prepared by reacting a halo-substituted compound with a mercaptide, $RS^{\ominus}M^{\oplus}$, to displace the halo substituent. Thioether-substituted hydantoins are disclosed in the Can. J. Research 27 (B), p. 421 and may be prepared according to the method disclosed therein.

The thioether-substituted 4-hydroxyquinazolines may be prepared by heating an ester of anthranilic acid with an RS-substituted amidine in an ethanolic solution of a sodium alkoxide. The thioether-substituted 2-hydroxypyridines may be prepared by reacting a 2-chloro-6-bromoalkylpyridine with a mercaptide, $RS^{\ominus}Na^{\oplus}$, to displace the bromo substituent followed by reacting with sodium benzylate and acid hydrolysis to yield the 2-hydroxy product. The thioether-substituted dehydrothiomorpholine-2-ones may be prepared by treating a mercaptoacetic acid ester with ammonia to form the corresponding amide which is ring-closed by reaction with chloroacetone/triethylamine to yield the 6-methyl-substituted ring system followed by bromination of the methyl group and reaction with a mercaptide to give the product. The 4-hydroxyquinolines may be prepared, for example, by reacting an RS-substituted aniline with diethylethoxymethylene malonate followed by heating in an inert solvent to give the ring-closed 3-$CO_2R$ intermediate which is treated with alkali, and if desired, decarboxylated. The compounds substituted with

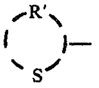

may be prepared, for example, by reacting a 2-chloroalkylthiophene with the selected mercapto-substituted compound and by displacement reactions using 2-bromothiophene. It will be appreciated that the above represent only some of the methods available for preparing thioether-substituted heterocyclic compounds and that other methods may be selected from those disclosed, for example, in The Chemistry of Heterocyclic Compounds, A. Weissberger, Wiley-Interscience.

In preparing thioether-substituted amino acids, mercapto-substituted amino acids may be treated with an alkylating agent to give the corresponding alkylthioether compound. The sulfonamido derivatives of the —S-containing amino acids may be prepared by reacting the acids with, e.g., p-toluene-sulfonyl chloride according to the procedure reported by E. W. McChesney et al., J. Amer. Chem. Soc., 59, p. 1116 (1937).

The alkanes containing a sulfonyl and a sulfinyl group may be synthesized from dithioalkanes wherein the thio groups are β to each other by treating with an oxidizing agent, e.g., potassium permanganate to yield the corresponding sulfide-sulfone and then treating the sulfide-sulfone with an oxidizing agent, such as, sodium metaperiodate to yield the sulfonyl-sulfinyl alkane. The 1,3-disulfonyl alkanes and cycloalkanes may be synthesized from the corresponding 1,3-dithio compounds by treating with an oxidizing agent, such as, peracetic acid, as described in Ber. 74, p. 1672 (1941), Ber. 32, p. 1375 (1899) and Tetrahedron Letters, 1962, p. 515. The alkanes containing a sulfonyl and a cyano group may be prepared according to the procedure of R. Dijkstra et al., Chem. Abs. 49:1153 gh (1955) by reacting a sodium alkylmercaptide with a chloro-substituted acetonitrile to yield the corresponding thio-nitrile which is then treated with an oxidizing agent, such as, hydrogen peroxide to give the product sulfonyl-cyano alkane. The alkanes containing a sulfonyl and an N-piperazinyl sulfonamido group may be prepared by reacting a sulfene with a piperazine using the procedure reported by G. Opitz et al., Angew, Chem. Internat. Edit. Vol. 5 (1966), p. 594. The thioether-substituted alkanes may be prepared by reacting the compounds containing a sulfonyl and a sulfinyl, cyano, sulfonamido or second sulfonyl group with the chloro-substituted derivative of the selected thioether substituent, e.g., R—S—$(CH_2)_2$—Cl.

Sulfonyl-piperazinylsulfonamido compounds, such as, those of formulas 69 and 70 form the subject matter of copending U.S. Patent application Ser. No. 564,166 of Richard B. Greenwald, now U.S. Pat. No. 3,976,647 issued Aug. 24, 1976. Sulfonyl-cyano compounds, such as, those of formulas 67 and 68 form the subject matter of copending U.S. Patent Application Ser. No. 575,584 of Alan L. Borror and Richard B. Greenwald, now U.S. Pat. No. 3,975,423 issued Aug. 17, 1976. 1,3-Disulfonylcycloalkanes, such as, those of formulas 57 to 64 form the subject matter of copending U.S. Patent Application Ser. No. 535,205 of Richard B. Greenwald filed Dec. 23, 1974, now U.S. Pat. No. 3,958,992 issued May 25, 1976.

The 5,6-disubstituted-2,4-dihydroxypyrimidines of formula V comprising the novel uracil compounds of the present invention may be prepared from uracils possessing a thioether group in one of the 5- or 6-positions and possessing a bromo or chloro group in the other by displacing the halo group with an alkyl mercaptan. Also, they may be prepared by reacting an alkyl mercaptan with a uracil substituted in the 5- and 6-positions with a chloroalkyl group. The 2,5-disubstituted-4,6-dihydroxypyrimidines of formula VI comprising the novel pseudo uracil compounds of the present invention may be prepared by reacting a thioether-substituted amidine with a thioether-substituted diethyl malonate using the procedures described in J. Chem. Soc. 1943, p. 388; J. Org. Chem. 18, p. 653; and J. Org. Chem. 17, p. 1320.

The following Examples are given to illustrate the present invention and are not intended to limit the scope thereof.

EXAMPLE 1

Preparation of the compound of formula (87)

Sodium (1.725 g., 0.075 m) was dissolved in 25 ml absolute ethanol. The solution was cooled in an ice bath and $CH_3SCH(COOC_2H_5)_2$ (3.51 g., 0.025 m) was added followed by the addition of $CH_3SCH_2C{=}NH \cdot HCl$
$NH_2$ (5.15 g., 0.025 m). The mixture was stirred in the cold for about 2 hours, then at room temperature for 3½ days, and finally heated at reflux for 1 hour. The ethanol was stripped in vacuo, the residue dissolved in water and the resulting dark brown solution acidified with conc. hydrochloric acid. A precipitate appeared and the mixture was cooled in an ice bath prior to filtering. The crude material was recrystallized from methylene chloride to give 1.0 g. of the title compound (melting range 258°-260° C. dec.).

| Analysis for $N_2O_2S_2C_7H_{10}$: | C | H | N | S |
|---|---|---|---|---|
| Calculated | 38.51 | 4.62 | 12.83 | 29.38 |
| Found | 38.61 | 4.61 | 12.72 | 29.19 |

The compounds of formulas (24) and (29) were prepared in the same manner given above using the appropriate thioether substituted malonate.

EXAMPLE 2

Preparation of the compound of formula (80)

(a) Barbituric acid (104 g., 0.81 m) was added to glacial acetic acid (320 ml). Acetic anhydride (104 ml) was added to the mixture followed by the addition of dimethylsulfoxide (72 ml). The mixture was heated at 100° C. for 4 hours. Within the first $\frac{1}{2}$ hour, the mixture solidified. The mixture was treated with 520 ml of water, cooled to room temperature and filtered. The crude material was washed with water, acetone, ethylene oxide, and after air-drying, 35 g. of the material was allowed to react with 95 ml of phosphorus oxychloride and 9.5 ml of N,N-dimethylaniline. The reaction mixture was heated at reflux for 24 hours, cooled to room temperature and decomposed with ice water. The light yellow solid was filtered and dried to give 20 g. of 2,4,6-trichloro-5-methylthiopyrimidine.

(b) The last-named compound (2.0 g.) was heated at reflux in 20 ml of 6N hydrochloric acid for 24 hours. The solid was filtered and recrystallized from 50% aqueous methylene chloride to afford about 400 mg. of 6-chloro-2,4-dihydroxy-5-methylthio pyrimidine as a white crystalline solid, melting point > 300° C.

(c) To 35 mls of 1 N aqueous sodium hydroxide was added mercaptoacetic acid sodium salt (1.26 g.) and the product of step b (1.92 g.). The resulting mixture was heated in an oil bath at about 80° C. After heating for about 22 hours, the reaction mixture was cooled in an ice bath and acidified with conc. hydrochloric acid to precipitate the product. The crude material was recrystallized from methylene chloride to afford 0.8 g. of the title compound (melting range 227°-229° C. dec.).

The compound of formula (79) was prepared using the above procedure expect that methylmercaptan was substituted for the sodium mercaptoacetate.

EXAMPLE 3

Preparation of the compound of formula (82)

A solution of 1.24 g. (0.022 mol) of potassium hydroxide in 25 ml of absolute ethanol was saturated with methylmercaptan. 5,6-di-chloromethyl-2,4-dihydroxypyrimidine, 2.1 g. (0.01 mol), was added all at once to the well stirred solution of mercaptan. After the initial vigorous reaction, the mixture was refluxed for 15 minutes and then cooled. The solvent was removed under reduced pressure and the residue treated with 25 ml of 10% hydrochloric acid. The solid was filtered, washed with water, and dried. Recrystallization from nitromethane gave 1.5 g. of the title compound (melting range 193°-195° C.

| Analysis for $C_8H_{13}N_2O_2S_2$: | C | H | N |
|---|---|---|---|
| Calculated | 41.41 | 5.21 | 12.08 |
| Found | 41.03 | 4.99 | 12.43 |

The compound of formula (81) was prepared according to the foregoing procedure except that ethylmercaptan was substituted for methylmercaptan.

The 5,6-di-chloromethyl-2,4-dihydroxypyrimidine employed above comprises the novel intermediate of the present invention. (According to the recent nomenclature adopted for uracil compounds by Chemical Abstracts, this compound would be named 4,5-di-chloromethyluracil.)

Functionalization of the 5-position of 2,4-dihydroxypyrimidine by employing formaldehyde and HCl to produce hydroxymethyl and chloromethyl derivatives is a well documented reaction and has been reported by W. A. Skinner et al., J. Org. Chem. 25, 149 (1960); J. A. Carbon, J. Org. Chem. 25, 1731 (1960); R. E. Cline et al., J. Amer. Chem. Soc., 81, 2521 (1959); J. H. Burckhalter et al., J. Amer., Chem. Soc., 82, 991 (1960); and D. Ziegler et al., Tetrahedron Lett., 1973, 2055. It has now been found that the chloromethylation reaction can be applied to 6-chloromethyl-2,4-dihydroxypyrimidine to produce in one step, an approximately 50% by weight yield of the 5,6-di-chloromethyl compound. This compound is a relatively stable crystalline solid which can be stored for long periods of time without decomposition and undergoes rapid displacement of chloride when treated with nucleophilic reagents to yield other difunctional 2,4-dihydroxypyrimidine derivatives such as the compounds of formulas (81) and (82) prepared above.

The subject di-chloromethyl compound having the formula

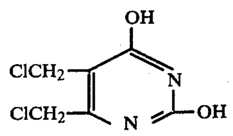

was prepared as follows:

A suspension of 16.0 g. (0.01 m) of 6-chloromethyl-2,4-dihydroxypyrimidine, 3.3 g. (0.011 m) of paraformaldehyde and 5 ml of 40% formalin solution in 30 ml of conc. hydrochloric acid was stirred while gaseous hydrogen chloride was passed through the slurry. The temperature was raised to 80° C. and maintained until a clear yellow solution was obtained. After precipitation began, about 1 hour, the temperature was lowered to 70° C. and the reaction continued for an additional hour. The mixture was chilled and filtered, and the white solid was washed with a small portion of cold water. After air-drying there was obtained 11.3 g. (53% by weight) of product (melting range 190°-194° C. dec.).

An analytical sample was obtained by crystallization from acetonitrile and required several hours of chilling.

| Analysis for $C_6H_6Cl_2N_2O_2$: | C | H | N |
|---|---|---|---|
| Calculated | 34.48 | 2.89 | 13.40 |
| Found | 34.96 | 3.00 | 13.69 |

It will be understood by those skilled in the art that the selection of a given silver halide solvent of the present invention will be based on the requirements of the particular photographic process and may be determined empirically. For example, for use in silver diffusion transfer processes, one will select a silver halide solvent which has a silver complexing and diffusion rate appropriate for obtaining a desired transfer image density within the desired specified time.

In formulating photographic processing compositions utilizing the above-described compounds, the compounds may be used singly or in admixture with each other or in admixture with other silver halide solvents. The total amount employed may vary widely depending upon the particular photographic system and should be used, for example, in a quantity sufficient for fixing a developed negative in conventional "tray" processing or in a quantity sufficient to give a satisfactory transfer print in diffusion transfer processes under the particular processing conditions employed.

Though the silver halide solvents of the present invention are broadly useful in a variety of photographic processes of the type in which water-soluble silver complexes are formed from the unreduced silver halide of a photoexposed and at least partially developed silver halide stratum, they find particular utility in diffusion transfer processes. A composition embodying the present invention specifically suitable for use in the production of transfer images comprises, in addition to the silver halide complexing agents of the above-described type, a suitable silver halide developing agent, preferably an organic developing agent. Examples of developing agents that may be employed include hydroquinone and substituted hydroquinones, such as, tertiary butyl hydroquinone, 2,5-dimethyl hydroquinone, methoxyhydroquinone, ethoxyhydroquinone, chlorohydroquinone; pyrogallol and catechols, such as, catechol, 4-phenyl catechol and tertiary butyl catechol; aminophenols, such as, 2,4,6-triamino-orthocresol; 1,4-diaminobenzenes, such as, p-phenylenediamine, 1,2,4-triaminobenzene and 4-amino-2-methyl-N,N-diethylaniline; ascorbic acid and its derivatives, such as, ascorbic acid, isoascorbic acid and 5,6-isopropylidene ascorbic acid, and other enediols, such as, tetramethylreductic acid; and hydroxylamines, such as, N,N-di(2-ethoxyethyl)hydroxylamine and N,N-di-(2-methoxyethoxyethyl)hydroxylamine.

In diffusion transfer processes, the processing composition if it is to be applied to the emulsion by being spread thereon in a thin layer also usually includes a viscosity-increasing reagent. The processing composition may comprise, for example, one or more silver halide solvents of the present invention, one or more conventional developing agents such as those enumerated above, an alkali such as sodium hydroxide, cesium hydroxide, or potassium hydroxide and a viscosity-increasing reagent such as a high molecular weight polymer, e.g., sodium carboxymethyl cellulose, hydroxyethyl cellulose or carboxymethylhydroxyethyl cellulose.

In one such transfer process, the processing solution is applied in a uniformly thin layer between the superposed surfaces of a photoexposed photosensitive element and an image-receiving element, for example, by advancing the elements between a pair of pressure-applying rollers. The elements are maintained in superposed relation for a predetermined period, preferably for a duration of about 15 to 120 seconds, during which exposed silver halide is reduced to silver and unreduced silver halide forms a water-soluble, complex salt which diffuses through the layer of solution to the image-receiving element there to be precipitated as an argental image. At the end of this period, the silver halide element is separated from the image-receiving element. Materials useful in such a transfer process are described in U.S. Pat. No. 2,543,181, issued in the name of Edwin H. Land on Feb. 27, 1951, and in numerous other patents.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers, etc.

The image-receiving element preferably includes certain materials, the presence of which, during the transfer process has a desirable effect on the amount and character of silver precipitated on the image-receiving element. Materials of this type are specifically described in U.S. Pat. Nos. 2,690,237 and 2,698,245, both issued in the name of Edwin H. Land on Dec. 28, 1954 and U.S. Pat. No. 3,671,241 of Edwin H. Land issued June 20, 1972.

Separating of the silver halide element from the image-receiving element may be controlled so that the layer of processing composition is removed from the image-receiving element or the layer of processing composition is caused to remain in contact with the image-receiving element, e.g., to provide it with a protective coating. Techniques which enable such results to be accomplished as desired are described in U.S. Pat. No. 2,647,056 issued to Edwin H. Land on July 28, 1953. In general, the processing reagents are selected so that traces remaining after the solidified processing layer has been separated from the silver image or which remain in said layer adhered as a protective coating on the silver image, as indicated above, are colorless or pale, so as not to appreciably affect the appearance of the image and to have little or no tendency to adversely react with the silver image.

The silver halide solvents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in U.S. application Ser. No. 383,196 of Edwin H. Land filed July 27, 1973 and in U.S. application Ser. No. 463,260 of Edwin H. Land filed Apr. 23, 1974. The subject compounds also find utility as silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489 of Ronald F. W. Cieciuch, Roberta R. Luhowy, Frank A. Meneghini and Howard G. Rogers.

The following example is given to illustrate the utility of the compounds of the present invention as photographic silver halide solvents and is not intended to be limiting.

EXAMPLE

A photosensitive silver halide emulsion on a support was exposed to a step wedge and processed by spreading a layer of processing composition approximately 0.0012 inch thick between the exposed emulsion and a superposed image-receiving element comprising a layer of regenerated cellulose containing colloidal palladium sulfide carried on a transparent support. The processing composition was prepared by adding a silver halide solvent of the present invention to the following formulation in a concentration of 5% by weight except where noted.

| | |
|---|---|
| Water | 814.0 g. |
| Potassium hydroxide | |
| (Aqueous 50% w/w solution) | 348.0 g. |
| Hydroxyethyl cellulose | 35.0 g. |
| Zinc acetate | 15.0 g. |
| Triethanolamine | 5.6 g. |
| Bis-N,N-methoxyethyl | |
| hydroxylamine | 50.0 g. |

After an imbibition period of approximately 1 minute, the developed silver halide emulsion was separated from the image-receiving element, and the maximum and minimum transmission densities were measured for the positive image.

The compounds added to the base formulation as silver halide solvents, and the density measurements obtained with each of the compounds are set forth in the following table.

TABLE I

| Compound | Density | |
|---|---|---|
| (Formula No.) | Maximum | Minimum |
| (1) | 2.04 | 0.57 |
| (2) | 1.41 | 0.26 |
| (3) | 1.90 | 0.27 |
| (4) | 2.20 | 0.61 |
| (5) | 2.10 | 0.08 |
| (6) | 0.78 | 0.04 |
| (7) | 1.20 | 0.01 |
| (9) | 2.21 | 0.33 |
| (10) | 1.24 | 0.12 |
| (11) | 1.20 | 0.17 |
| (12) | 0.94 | 0.02 |
| (13) | 1.85 | 0.68 |
| (14) | 1.70 | 0.44 |
| (15) | 2.69 | 0.51 |
| (20) | 2.25 | 0.23 |
| (22) | 1.24 | 0.12 |
| (23) | 1.24 | 0.13 |
| (24) | 2.22 | 0.16 |
| (25) | 2.40 | 0.24 |
| (26) | 2.19 | 0.35 |
| (27) | 1.66 | 0.05 |
| (28) | 2.09 | 0.15 |
| (29) | 2.95 | 0.79 |
| (31) | 2.05 | 0.12 |
| (36) | 1.00 | 0.01 |
| *(80) | 1.14 | 0.12 |
| (82) | 1.60 | 0.50 |
| (87) | >2.50 | 0.20 |

*Added to formulation in a concentration of 10% by weight.

In a visual comparison between the positive images obtained with the compounds listed in the foregoing table and a positive image obtained with uracil, it was observed that the uracils and pseudo uracils of the present invention gave positive images having more neutral tone than the positive image produced with uracil.

The photographic procedure described above was repeated employing other classes of silver halide solvents of the present invention which were added to the same base formulation in a concentration of 5% by weight. The compounds employed and the maximum and minimum transmission densities measured for each of the compounds are set forth in TABLE II below.

TABLE II

| Compound | Density | |
|---|---|---|
| (Formula No.) | Maximum | Minimum |
| (21) | 1.51 | 0.96 |
| (43) | 1.72 | 0.37 |
| (45) | 0.80 | 0.41 |
| (49) | 0.86 | 0.10 |
| (54) | 0.90 | 0.58 |
| (57) | 1.20 | 0.10 |
| (65) | 2.53 | 1.80 |
| (68) | 2.36 | 1.76 |
| (76) | 1.66 | 0.22 |

It will be apparent that the relative proportions of the subject silver halide solvents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the processing compositions, other components as commonly used in the photographic art.

Rather than being dissolved in the aqueous alkaline processing composition prior to application thereof to an exposed silver halide emulsion, it is also contemplated that the silver halide solvents of the present invention may be disposed prior to exposure in a layer or layers of the photographic film unit, e.g., by placing them behind a silver halide emulsion layer in the photosensitive element. In this instance, the processing composition containing the silver halide solvent is formed by application to the photosensitive element of an aqueous alkaline solution capable of solubilizing the silver halide solvent. Likewise, the developing agent or auxiliary developing agent, depending upon the particular photographic process, also may be disposed in a layer or layers of the film unit and solubilized upon application of an aqueous alkaline solution. In diffusion transfer processes, the subject silver halide solvents usually are contained in the processing composition.

Since certain changes may be made in the above compositions and processes without departing from the scope of the invention herein involved, it is intended that all matter contained in the above description should be interpreted as illustrative and not in a limiting sense.

What is claimed is:

1. A compound of the formula

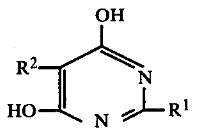

wherein one of $R^1$ and $R^2$ is $\text{-}(CH_2)_xSR^3$ and the other of said $R^1$ and $R^2$ is $\text{-}(CH_2)_ySR^3$ wherein $R^3$ is alkyl, x is a whole number 0 or 1 and y is a whole number from 0 to 5.

2. A compound as defined in claim 1 wherein said x is 0.

3. A compound as defined in claim 1 wherein said x is 1.

4. A compound as defined in claim 1 wherein said y is 1.

5. A compound as defined in claim 1 wherein $R^3$ is methyl.

6. The compound

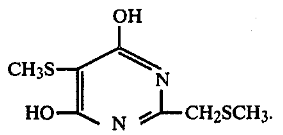

7. The compound

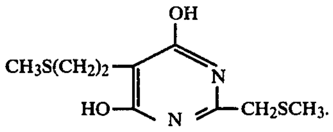

8. The compound

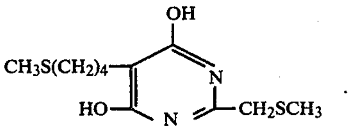

9. A compound of the formula

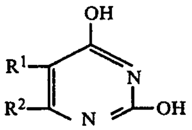

wherein one of $R^1$ and $R^2$ is $\text{-}(CH_2)_x\text{-}SR^3$ and the other of said $R^1$ and $R^2$ is $\text{-}(CH_2)_y\text{-}SR^3$ wherein $R^3$ is alkyl, x is a whole number 0 or 1 and y is a whole number from 0 to 5.

10. A compound as defined in claim 9 wherein x is 0.

11. A compound as defined in claim 9 wherein x is 1.

12. A compound as defined in claim 10 wherein y is 0.

13. A compound as defined in claim 11 wherein y is 1.

14. A compound as defined in claim 9 wherein $R^3$ is methyl.

15. A compound as defined in claim 9 wherein $R^3$ is ethyl.

16. The compound

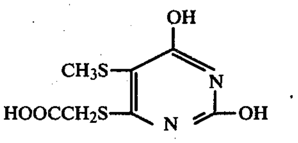

17. The compound

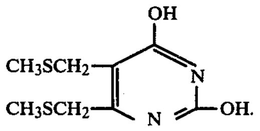

18. The compound

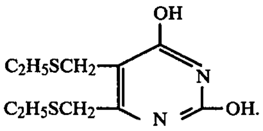

19. The compound

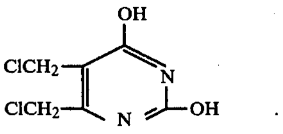

* * * * *